United States Patent [19]

Brown et al.

[11] 4,024,160

[45] May 17, 1977

[54] SUBSTITUTED 2-AMINO CHROMONES AND PROCESS FOR THE PREPARATION THEREOF

[75] Inventors: Richard E. Brown, Hanover; David M. Lustgarten, Dover, both of N.J.

[73] Assignee: Warner-Lambert Company, Morris Plains, N.J.

[22] Filed: Oct. 3, 1975

[21] Appl. No.: 619,150

Related U.S. Application Data

[62] Division of Ser. No. 532,417, Dec. 13, 1974, Pat. No. 3,932,466.

[52] U.S. Cl. ............................ 260/345.2; 260/345.5; 260/479 R; 424/283
[51] Int. Cl.² .................. C07D 311/02; C07D 311/72
[58] Field of Search .......... 260/345.2, 345.5, 345.1

[56] References Cited

UNITED STATES PATENTS

| | | | |
|---|---|---|---|
| 2,449,038 | 9/1948 | Hultquist | 260/344.6 |
| 3,801,602 | 4/1974 | Scheuermann et al. | 260/345.2 |
| 3,825,574 | 7/1974 | Brown | 260/345.2 |
| 3,853,921 | 12/1974 | Klutchko et al. | 260/345.2 |
| 3,862,143 | 1/1975 | Klutchko et al. | 260/345.2 |

*Primary Examiner*—James O. Thomas, Jr.
*Assistant Examiner*—Nicky Chan
*Attorney, Agent, or Firm*—Albert H. Graddis; Frank S. Chow; Anne M. Kelly

[57] ABSTRACT

This invention relates to substituted 2-amino chromones of the general structure I:

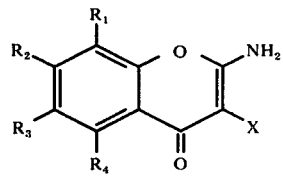

wherein $R_1$, $R_2$, $R_3$, and $R_4$ may be hydrogen, hydroxy, lower alkyl or lower alkoxy of 1–6 carbon atoms, halogen such as chloro or bromo, or aryl such as phenyl, and X may be cyano or carboxamido. Two novel procedures for preparing substituted 2-amino chromones having the Formula I, starting with salicylic acid or substituted salicylic acid, are described. The compounds of this invention are active in the prevention of allergic and asthmatic reactions in mammals.

5 Claims, No Drawings

SUBSTITUTED 2-AMINO CHROMONES AND PROCESS FOR THE PREPARATION THEREOF

This is division of application Ser. No. 532,417, filed Dec. 13, 1974, now U.S. Pat. No. 3,932,466, published Jan. 13, 1976.

DESCRIPTION OF THE PRIOR ART

Benzopyran and chromone structures having a cyano group in the 3-position are known in the art.

For example, in U.S. Pat. No. 2,449,038, a method for preparing 3-cyano-4-hydroxy coumarin (also known as 3-cyano-benzotetronic acid which can exist either in the 4-hydroxy or 4-keto form) is disclosed: acetylsalicylyl chloride is reacted with ethyl cyanoacetate. All compounds prepared according to the method disclosed in U.S. Pat. No. 2,449,038 must contain a 2-keto substituent in addition to the 3-cyano and 4-hydroxy or 4-keto groups. Glozman, S. M. et al. disclose the synthesis of 2-amino chromone derivatives in Kim. Farm. Zh 5: 17–21 (1971). And Checchi, S. et al., in Gazz. Chim. Ital. 96: 874–884 (1966) demonstrate conversion of 2-keto-3-cyanochromone to 2-aminochromone.

In U.S. Pat. No. 3,825,574, U.S. Pat. No. 3,853,921 and in U.S. Ser. No. 312,154, filed Dec. 4, 1972, now U.S. Pat. No. 3,862,143 published Jan. 21, 1975, 3-cyano-2-substituted chromones and the preparation thereof are disclosed. The 2-substituent on the chromone compounds of these last-mentioned patents may be hydrogen, lower alkyl, fluorinated lower alkyl, lowr alkoxycarbonyl, carboxy, or lower alkyl carboxylic acid.

Thus, none of aforementioned prior art discloses a benzopyran or a chromone structue having a 2-amino as well as a 3-cyano substituent; nor has any process for the preparation of such 2-amino-3-cyano-chromone structures been disclosed.

DESCRIPTION OF THE SPECIFIC EMBODIMENTS

This invention relates to novel substituted 2-aminochromones of the general structue I:

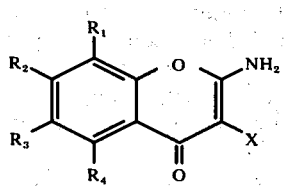

In the above structure, $R_1$, $R_2$, $R_3$, and $R_4$ may be hydrogen, hydroxy, lower alkyl or lower alkoxy of 1–6 carbon atoms, halogen such as chloro or bromo, or aryl such as phenyl, and X may be cyano or carboxamido.

The compounds of this invention may be prepared by either of two methods. In the first method, salicylic acid or a substituted salicylic acid of structure II is used as starting material.

In structure II, $R_1$, $R_2$, $R_3$, and $R_4$ are as defined for structure I.

In the first step, the free hydroxyl groups of the substituted salicylic acid are protected by conversion to an acyloxy group as acetoxy to give a structure according to structure III.

In structure III, $R_1$, $R_2$, $R_3$, and $R_4$ may be hydrogen, lower alkanoyloxy of 2–6 carbon atoms, such as acetoxy, lower alkyl or lower alkoxy of 1–6 carbon atoms, halogen such as bromo or chloro, or aryl such as phenyl. $R_5$ may be lower alkyl of 1 to 5 carbon atoms.

Among the reagents which may be used for this conversion are acetyl chloride or acetic anhydride.

In the second step, the acetoxy derivative according to structure III is converted to its acid chloride of structure IV in which $R_1$, $R_2$, $R_3$, $R_4$, and $R_5$ are as defined for structure III. Among the reagents which may be used for this reaction are thionyl chloride, oxalyl chloride or, preferably, phosphorous pentachloride.

In the third step, the acid chloride according to structure IV is reacted with malonoitrile in the presence of a basic catalyst and solvent to give the compound according to structure I wherein X is cyano. Among the basic catalysts which may be used there may be mentioned triethylamine, alkali metal hydrides such as sodium hydride, alkali metal hydroxides, amides of the formula M—NH$_2$ wherein M is an akali metal (potassium amide and the like), and alkoxides of the formula R—O—M wherein R is a lower alkyl group of 1 to 6 carbon atoms and M is an alkali metal. Among the suitable solvents which may be used are water, benzene, toluene, tetrahydrofuran, and dimethylformamide. Naturally, the basic catalyst and solvent selected must be compatable, i.e., non-reactant with one another. Preferably, a combination of an alkali metal hydroxide, such as sodium hydroxide, in aqueous medium is used.

In the second method by which the compounds of this invention may be prepared, the salicylic acid of structure II is esterified with a lower molecular weight alcohol, such as methanol or ethanol, to give a compound according to structure V wherein $R_1$, $R_2$, $R_3$, and $R_4$ are as defined for structure I and wherein $R_6$ may be lower alkyl of 1 to 6 carbon atoms. This esterification may be carried out by procedures which are standard to the art.

The ester V thus prepared is reacted with malonontrile in the presence of an inert solvent and a strong base to afford the compound of structure I wherein X is cyano. Suitable bases for this reaction are alkali metal hydrides, such as sodium hydride, amides of the formula M—NH$_2$ wherein M is an alkali metal (potassium amide and the like) and alkoxides of the formula R—O—M wherein R is a 1 to 6 carbon atom lower alkyl group and M is an alkali metal. Suitable solvents for this reaction are benzene, toluene, tetrahydrofuran, dimethylformamide and dimethylsulfoxide.

In order to prepare those compounds according to structure I wherein X is carboxamido, the compound according to structure I wherein X is cyano is subjected to an acid catalyzed hydrolysis step. Among the acids which may be used for this reaction are mineral acids as hydrochloric, phosphoric, or, preferably, sulfuric.

In this invention the salicylic acids, esters, acid chlorides and acetoxy derivatives used as starting materials or intermediates are all commercially available or are compounds easily prepared by known methods described the literature, as for example those methods described in A. R. Fersht and A. J. Kirby, J. Am. Chem. Soc., 89: 4853–4857 (1967); P. Moses and R. Dahlbom, Aata Chem. Scand. 19: 823–832; and J. Sieben, Ann. 367: 218–245 (1909).

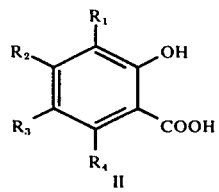
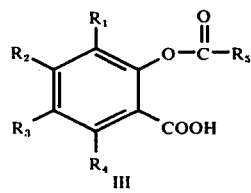
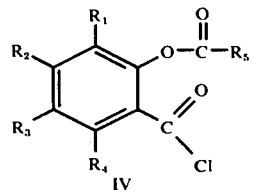
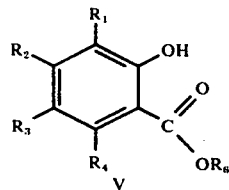

The compounds of this invention are active in the prevention of allergic and asthmatic reactions in mammals. For example, in tests conducted by the procedures described in I. Mota, Life Sciences, Vol. 4; No. 7, 465–474 (1963) and Z. Ovary et al., Proc. Soc. Exptl. Biol. Med., 81: 584–586 (1952), these compounds are capable of protecting rats from allergic and asthmatic reactions at a dose level of 5–100 mg/kg, when administered parenterally or orally. This dosage may be varied depending upon the severity of the condition, the age, weight, and sex of the mammal being treated, and the route of administration.

In use, the compounds of Formula I may be combined with a parenterally acceptable vehicle, such as gum tragacanth, in saline suspension, to provide dosage forms suitable for parenteral administration; or they may be combined with pharmaceutical diluents such as lactose, cornstarch, and the like and formulated into tablet or capsule dosage forms. In order to enhance their therapeutic spectrum, the compounds of Formula I may be combined with sympathomimetic agents such as isoproterenol or combined with steroids such as cortisone and its derivatives.

In all of the above Formulas I, II, III, IV, and V, the R group definitions may be more fully described as follows: the term "lower alkyl" is meant to include lower aliphatic hydrocarbons having 1 to 6 carbon atoms in the carbon chain, such as methyl, ethyl, propyl, isopropyl, butyl or isobutyl. This definition for lower alkyl also applies to the lower alkyl portion of "lower alkoxy". The term "lower acyloxy" is meant to include lower alkyl carboxylic acids wherein "lower alkyl" has the aforementioned meaning. The term "halogen" is meant to include bromine, chlorine, iodine and fluorine.

To further illustrate the practice of this invention, the following examples are included:

EXAMPLE 1

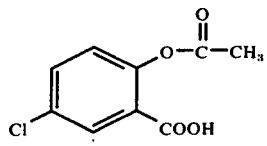

2-Acetoxy-5-chlorobenzoic acid

A mixture of 86 g (0.5 mole) of 5-chloro salicylic acid and 102 g (1.0 mole) of acetic anhydride are warmed to 40° C. With stirring, 5 drops of conc. sulfuric acid are added, which causes an exothermic reaction. The mixture is stirred for ½ hour at 60° C. then poured into ice. The solid is filtered, washed with water and air dried, mp 146°–8° C, and is used as is for the next step.

EXAMPLE 2

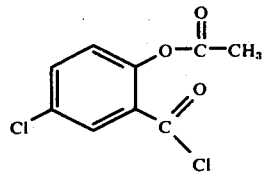

2-Acetoxy-5-chlorobenzoyl chloride

To a suspension of 21.4 g (0.1 mole) of 2-acetoxy-5-chlorobenzoic acid in 100 ml of refluxing benzene is added in portions over 1 hour 20.8 g (0.1 mole) of phosphorous pentachloride. The clear solution is refluxed for 1 hour, then concentrated to dryness. The residue is distilled, bp 112° C at 0.1 mm to give a clear oil which solidified on standing, mp 35°–8° C.

EXAMPLE 3

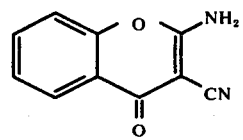

2-Amino-4-oxo-4H-1-benzopyran-3-carbonitrile

A mixture of 6.6 g (0.1 mole) of malononitrile, 50 g of ice, 5 ml of 20% sodium hydroxide and 9.9 g (0.5 mole) of 2-acetoxy benzoyl chloride is stirred vigorously for 10 minutes. Second portions of mlononitrile and 20% sodium hydroxide are added, the mixture is stirred another 10 minutes, then warmed to 40° C. With stirring, there is added 50% potassium hydroxide solution in 5 ml increments until the solution becomes clear. The solution is cooled, acidified with conc. HCl, and the solid filtered and washed with water and air dried, mp 315°–20° C.

Anal. calcd for $C_{10}H_6N_2O_2$: C, 64.52; H, 3.25; N, 15.05. Found: C, 64.32; H, 3.33; N, 15.14.

EXAMPLE 4

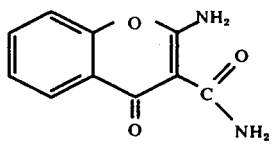

2-Amino-4-oxo-4H-1-benxopyran-3-carboxamide

A mixture of 1.5 g of 2-amino-4-oxo-4H-1-benzopyra-3-carbonitrile and 7 ml of 80% sulfuric acid is heated for 1 hour on the steam bath. The mixture is cooled, poured into water, and the solid filtered and recrystallized from ethanol, mp 264°–6° C.

Anal. calcd for $C_{10}H_8N_2O_3$: C, 58.82; H, 3.95; N, 13.72. Found: C, 58.78; H, 3.88; N, 13.50.

EXAMPLE 5

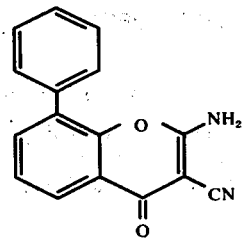

2-Amino-4-oxo-8-phenyl-4H-1-benzopyran-3-carbonitrile

A mixture of 5.0 g (.11 mole) of 57% sodium hydride-mineral oil and 11.4 g (0.05 mole) of methyl-3-phenyl salicylate in 400 ml dimethylformamide is stirred for 5 minutes, then 6.6 g (0.1 mole) of malononitrile is added. The mixture is stirred overnight at room temperature, then refluxed for 4 hours, cooled, and poured into water. The solution is acidified and the solid filtered and recrystallized from ethanol-water, mp 217°–19° C.

Anal. calcd for $C_{16}H_{10}N_2O_2$: C, 73.27; H, 3.84; N, 10.68. Found: C, 71.71; H, 4.07; N, 10.19.

EXAMPLE 6

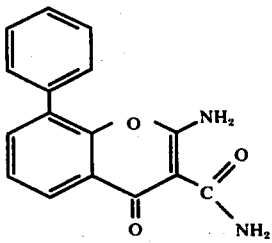

2-Amino-4-oxo-8-phenyl-4H-1-benzopyran-3-carboxamide

In the same way as described in Example 4, 2-amino-4-oxo-8-phenyl-4h-1-benzopyran-3-carbonitrile is hydrolyzed, mp 233°–5° C after recrystallization from ethanol-water.

Anal. calcd for $C_{16}H_{12}N_2O_3$: C, 68.56; H, 4.32; N, 10.00. Found: C, 68.01; H, 4.37; N, 9.57.

EXAMPLE 7

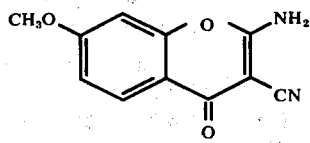

2-Amino-7-methoxy-4-oxo-4H-1-benzopyran-3-carbonitrile

In the same way as described in Example 5, methyl-4-methoxy salicylate and malononitrile are reacted to give crystals, mp 300° C.

Anal. Calcd for $C_{11}H_8N_2O_3$: C, 61.11; H, 3.73; N, 12.96. Found: C, 60.93; H, 3,76; N, 12.88.

EXAMPLE 8

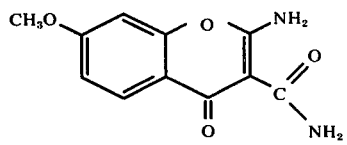

2-Amino-7-methoxy-4-oxo-4H-1-benzopyran-3-carboxamide

In the same way as described in Example 4, 2-amino-7-methoxy-4-oxo-4H-1-benzopyran-3-carbonitrile is hydrolyzed, mp 265°–6° C.

Anal calcd for $C_{11}H_{10}N_2O_4$: C, 56.41; H, 4.30; N, 11.96. Found: C, 56.29; H, 4.37; N, 11.58.

EXAMPLE 9

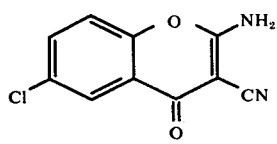

2-Amino-6-chloro-4-oxo-4H-1-benzopyra-3-carbonitrile

In the same way as described in Example 3, 2-acetoxy-5-chlorobenzoyl chloride and malononitrile are reacted to give crystals, mp 340° C.

Anal. calcd for $C_{10}H_5ClN_2O_2$: C, 54.44; H, 2.29; N, 12.70. Found: C, 54.24; H, 2.38; N, 12.42.

EXAMPLE 10

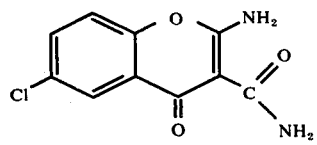

2-Amino-6-chloro-4-oxo-4H-1-benzopyran-3-carboxamide

In the same way as described in Example 4, 2-amino-6-chloro-4-oxo-4H-1-benzopyran-3-carbonitrile is hydrolyzed to give crystals, mp 320° C after recrystallization from acetic acid.

Anal. calcd for $C_{10}H_7ClN_2O_3$: C, 50.33; H, 2.96; N, 11.74. Found: C, 50.12; H, 2.90; N, 11.66.

EXAMPLE 11

-continued

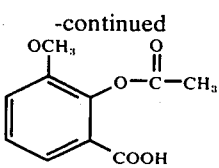

2-Acetoxy-3-methoxy benzoic acid

In the same way as described in Example 1, 3-methoxy salicylic acid is acetylated to give crystals, mp 139°–40° C which are used directly for the next step.

EXAMPLE 12

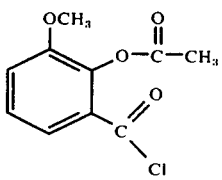

2-Acetoxy-3-methoxy benzoyl chloride

In the same way as described in Example 2, 2-acetoxy-3-methoxy benzoic acid is converted to its acid chloride. The solid product, mp 51°–4° C, is used directly for the next step.

EXAMPLE 13

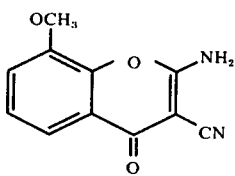

2-Amino-4-oxo-8-methoxy-4H-1-benzopyran-3-carbonitrile

In the same way as described in Example 3, 2-acetoxy-3-methoxy-benzoyl chloride and malononitrile are reacted to give a crystalline product, mp 300° C.
Anal. calcd for $C_{11}H_8N_2O_3$: C, 61.11; H, 3.73; N, 12.96. Found: C, 60.93; H, 3.81; N, 12.84.

EXAMPLE 14

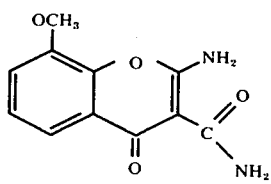

2-Amino-4-oxo-8-methoxy-4H-1-benzopyran-3-carboxamide

In the same way as described in Example 4, 2-amino-4-oxo-8-methoxy-4H-1-benzopyran-3-carbonitrile is hydrolyzed to give crystals, mp 302° C after recrystallization from methanol.
Anal. calcd. for $C_{11}H_{10}N_2O_4$: C, 56.41; H, 4.30; N, 11.96. Found: C, 56.25; H, 4.42; N, 12.05.

EXAMPLE 15

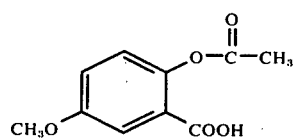

2-Acetoxy-5-methoxy benzoic acid

In the same way as described in Example 1, 5-methoxy salicylic acid is acetylated to give a solid product, mp 155°–7° C, which is used as is for the next step.

EXAMPLE 16

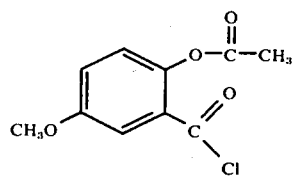

2-Acetoxy-5-methoxy benzoyl chloride

In the same was as described in Example 2, 2-acetoxy-5-methoxy benzoic acid is converted to its acid chloride. The product has bp 127°–30° C at 0.4 mm. The distillate becomes a waxy solid which is used directly for the next step.

EXAMPLE 17

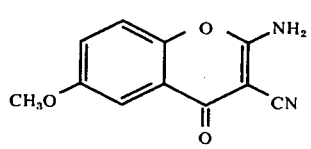

2-Amino-4-oxo-6-methoxy-4H-1-benxopyran-3-carbonitrile

In the same way as described in Example 3, 2-acetoxy-5-methoxy benzoylchloride and malononitrile are reacted to give crystals, mp 320° C after recrystallization from methanol.
Anal. calcd for $C_{11}H_8N_2O_3$: C, 61.11; H, 3.73; N, 12.96. Found: C, 61.09; H, 3.80; N, 13.25.

EXAMPLE 18

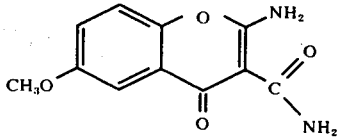

2-Amino-4-oxo-6-methoxy-4H-1-benzopyran-3-carboxamide

In the same way as described in Example 4, 2-amino-4-oxo-6-methoxy-4H-1-benzopyran-3-carbonitrile is hydrolyzed to give crystals, mp 270° C after recrystallization from methanol.

Anal. calcd. for $C_{11}H_{10}N_2O_4$: C, 56.41; H, 4.30; N, 11.96. Found: C, 56.19; H, 4.40; N, 11.80.

We claim:

1. A process for the production of a compound of the Formula I:

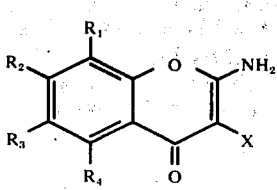

wherein $R_1$, $R_2$, $R_3$ and $R_4$ each represent hydrogen, hydroxy, lower alkyl of 1 to 6 carbon atoms, lower alkoxy of 1 to 6 carbon atoms, halogen or phenyl; and X represents carboxamido, which comprises:

A. Treating a compound of the Formula II:

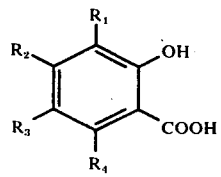

wherein $R_1$, $R_2$, $R_3$, and $R_4$ are as defined above in Formula I with an acid chloride or an acid anhydride to convert all free hydroxyl groups to acyloxy groups and obtain a compound of the Formula III:

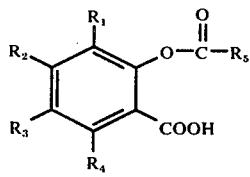

wherein $R_1$, $R_2$, $R_3$, and $R_4$ each represent hydrogen, lower alkyl of 1 to 6 carbon atoms, lower alkoxy of 1 to 6 carbon atoms, lower alkanoyloxy of 2 to 6 carbon atoms, halogen, or phenyl; and $R_5$ represents 1 to 5 carbon lower alkyl;

B. Treating Compound III with a reagent selected from the group consisting of thionyl chloride, oxalyl chloride, and phophorous pentachloride to obtain a compound of the Formula IV:

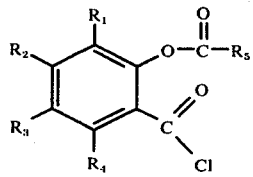

wherein $R_1$, $R_2$, $R_3$, $R_4$, and $R_5$ are as defined above in formula III;

C. Treating a solution of Compound IV with malononitrile in the presence of a basic catalyst selected from the group consisting of triethylamine, alkali metal hydrides, alkali metal hydroxides, amides of the formula M—$NH_2$ wherein M is an alkali metal, and alkoxides of the formula R—O—M wherein R is a 1 to 6 carbon lower alkyl group and M is an alkali metal, to obtain a compound of the formula:

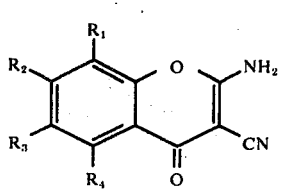

wherein $R_1$, $R_2$, $R_3$, and $R_4$ are as defined above in Formula I, which is subjected to acid catalysed hydrolysis to obtain Compound I wherein X is carboxamido.

2. A process according to claim 1 wherein, in Step A, an acid derivative selected from the group consisting of acetyl chloride and acetic anhydride is used.

3. A process according to claim 1 wherein, in Step C, the solvent is selected from the group consisting of water, benzene, toluene, tetrahydrofuran and dimethylformamide.

4. A process according to claim 1 wherein, in Step C, an aqueous solution of sodium hydroxide is used as the solvent and the basic catalyst.

5. A process for the production of a compound of the Formula I:

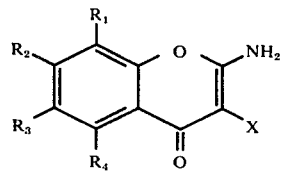

wherein $R_1$, $R_2$, $R_3$, and $R_4$ each repesent hydrogen, hydroxy, lower alkyl of 1 to 6 carbon atoms, lower alkoxy of 1 to 6 carbon atoms, halogen or phenyl; and X represents cyano, which comprises:

A. Treating a compound of the formula II:

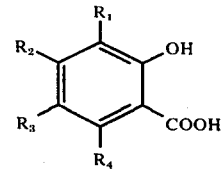

wherein $R_1$, $R_2$, $R_3$, and $R_4$ are as defined above in Formula I with an acid chloride or an acid anhydride to convert all free hydroxyl groups to acyloxy groups and obtain a compound of the Formula III:

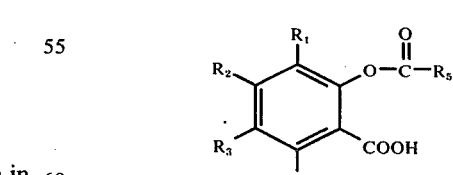

wherein $R_1$, $R_2$, $R_3$, and $R_4$ each represent hydrogen, lower alkyl of 1 to 6 carbon atoms, lower alkoxy of 1 to 6 carbon atoms, lower alkanoyloxy of 2 to 6 carbon atoms, halogen, or phenyl; and $R_5$ represents 1 to 5 carbon lower alkyl;

B. Treating Compound III with a reagent selected from the group consisting of thionyl chloride, oxalyl chloride, and phophorous pentachloride to obtain a compound of the Formula IV:

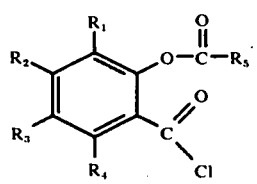

wherein $R_1$, $R_2$, $R_3$, $R_4$, and $R_5$ are as defined above in Formula III;

C. Treating a solution of Compound IV with malononitrile in the presence of a basic catalyst selected from the group consisting of triethylamine, alkali metal hydrides, alkali metal hydroxides, amides of the formula M—$NH_2$ wherein M is an alkali metal, and alkoxides of the formula R—O—M wherein R is a 1 to 6 carbon lower alkyl group and M is an alkali metal, to obtain Compound I wherein X is cyano.

* * * * *